United States Patent
Järverud et al.

(10) Patent No.: US 8,060,203 B2
(45) Date of Patent: Nov. 15, 2011

(54) METHOD AND APPARATUS FOR DETERMINING VARIATION OVER TIME OF A MEDICAL PARAMETER OF A HUMAN BEING

(75) Inventors: Karin Järverud, Solna (SE); Kjell Noren, Solna (SE)

(73) Assignee: St. Jude Medical AB, Jarfalla (SE)

( * ) Notice: Subject to any disclaimer, the term of this patent is extended or adjusted under 35 U.S.C. 154(b) by 248 days.

(21) Appl. No.: 12/438,397

(22) PCT Filed: Aug. 28, 2006

(86) PCT No.: PCT/SE2006/000985
§ 371 (c)(1), (2), (4) Date: Feb. 23, 2009

(87) PCT Pub. No.: WO2008/026970
PCT Pub. Date: Mar. 6, 2008

(65) Prior Publication Data
US 2010/0249864 A1   Sep. 30, 2010

(51) Int. Cl.
*A61N 1/00* (2006.01)
(52) U.S. Cl. .................................................. 607/17
(58) Field of Classification Search .............. 600/12, 600/324, 407, 500, 509, 521, 544, 547; 607/11, 607/14, 17, 19, 2, 4–6, 9; 702/66; 705/2
See application file for complete search history.

(56) References Cited

U.S. PATENT DOCUMENTS

| | | | |
|---|---|---|---|
| 5,792,197 A | 8/1998 | Nappholz | |
| 7,082,329 B2* | 7/2006 | Jarverud | 607/17 |
| 7,171,271 B2 | 1/2007 | Koh et al. | |
| 2003/0233048 A1* | 12/2003 | Silverman et al. | 600/500 |
| 2005/0124900 A1 | 6/2005 | Stadler et al. | |
| 2005/0137489 A1 | 6/2005 | Jackson et al. | |
| 2006/0149327 A1 | 7/2006 | Hedberg et al. | |
| 2009/0099475 A1* | 4/2009 | Bjorling | 600/547 |

\* cited by examiner

*Primary Examiner* — George Manuel
*Assistant Examiner* — Robert Wieland
(74) *Attorney, Agent, or Firm* — Schiff Hardin LLP

(57) ABSTRACT

An apparatus for determining variation over time of a medical parameter of a human being obtained from a sensed signal has a sensor implantable in the human being for sensing the signal. A comparator compares at least one characteristic property, derived from the sensed signal obtained for at least one predetermined first level of activity of the human being, with corresponding reference property of a sensed reference signal, obtained for a predetermined reference level of activity of the human being, for determining a relation between the characteristic property of the sensed signal and the reference property. A trend determining unit determines trends in the medical parameter by analyzing the relation between the characteristic property of the sensed signal obtained at different times and the reference property. A corresponding method also function an implant for heart failure diagnostics also function as described. A sensor is then arranged to pick up dynamic mechanical information from the heart of the human being and generate a corresponding signal. A heart stimulator includes such an implant and a control unit arranged to control stimulation of the heart depending on determined trends in the medical parameter.

20 Claims, 4 Drawing Sheets

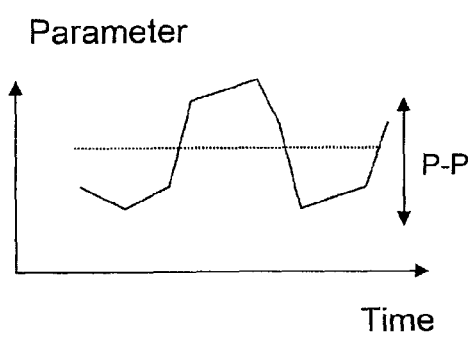
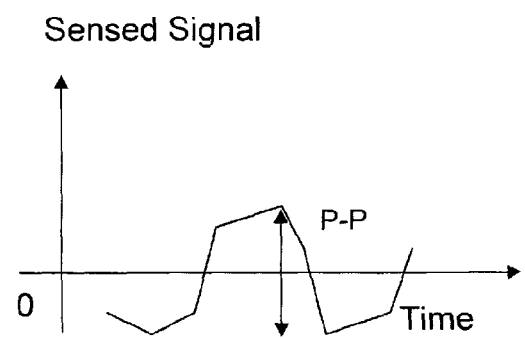
Fig. 1
Fig. 2

METHOD AND APPARATUS FOR DETERMINING VARIATION OVER TIME OF A MEDICAL PARAMETER OF A HUMAN BEING

BACKGROUND OF THE INVENTION

1. Field of the Invention

The present invention relates to an apparatus and a method for determining variation over time of a medical parameter of a human being. The invention also relates to an implant for heart failure diagnostics comprising such an apparatus as well as a heart stimulator including such an implant to be used for controlling the stimulation.

2. Description of the Prior Art

The progress of medical parameters over time needs to be closely monitored to minimize patient pain, discomfort and hospitalization. Thus, as an example, for this purpose the progress of the cardiac function must be closely monitored over time as the cardiac failure condition changes.

An example of long term monitoring of a medical parameter is disclosed in U.S. Pat. No. 5,792,197. An implantable rate responsive pacemaker uses a physiological demand parameter to classify the patient's degree of congestive heart failure. The parameter is monitored for extended time periods to determine the levels for this parameter for different levels of physical activity of the patient.

Implantable sensors are most often incapable of sensing static information. The signal can be described as being dynamic. Due to this, it is of particular interest to be able to retrieve information for long term monitoring from dynamic sensor signals obtained from implanted sensors.

SUMMARY OF THE INVENTION

An object of the present invention is to provide a technique for determining variations over time—trending—of a medical, diagnostic parameter obtained from the sensed dynamic signal of an implanted sensor.

The above object is achieved in accordance with the present invention by an apparatus for determining variation over time of a medical parameter of a human being obtained from a sensed signal, having a sensor that is implantable in the human being for sensing the aforementioned signal. A controller operates the sensor to obtain a sensed referenced signal for a predetermined reference level of activity of the human being. The controller also operates the sensor to obtain the sensed signal at a number of different times for at least one predetermined level of activity of the human being. A comparator is supplied with the sensed signal and the sensed reference signal, and determines a relation between a characteristic property, derived from the sensed signal, and the same property derived from the reference sensed signal. A trend determining unit is supplied with this relation, and determines therefrom a trend in a medical parameter of the human being by analyzing the aforementioned relation.

Since some implanted dynamic sensors do not pick up any absolute signal magnitudes, i.e. no DC signal, but only variations in the signal, i.e. AC signals, some sort of pseudo-zero-level or pseudo-reference must be created for the comparisons from time to time needed for the trend analysis as specified in the above mentioned claims. The relations determined between characteristic properties of the sensor signal at the first level of activity and the reference level of activity of the patient can be stored and displayed at follow-up or distributed continuously to a central diagnostic unit of a hospital for evaluation.

According to advantageous embodiments of the invention the implantable sensor is a piezoelectric pressure sensor. In his sensor, which is primarily intended for cardiac use, the indifferent electrode lead is coated by piezoelectric material, such that the output signal of the sensor contains both electric and pressure information. The dynamic pressure information includes several components and information of interest can be retrieved by suitable filtering.

The reference signal is sensed for a predetermined reference level of activity of the patient in question. The term activity in this context includes both actual physical activity of the patient and his or her body position or posture. In principle any well-defined level of activity of the patient can be used as reference level of activity, e.g. the human being lying down resting or being at maximum activity. However, according to an advantageous embodiment of the apparatus according to the invention the predetermined reference level of activity of the patient is a situation of minimum activity. It is particularly suitable to use the signal sensed during night-time when the patient is at sleep as reference signal, because posture changes during night-time do not cause problems as the reference signal can be averaged over some time with the patient at sleep. In its simplest form this can be realized by a clock-triggered analysis, for instance between 00.00 and 02.00 am. In a more advanced solution combined informations from a clock, activity and posture sensors can be used for reference signal determination.

According to still another advantageous embodiment of the apparatus according to the invention the comparing means is arranged to determine relations between the characteristic property of the sensed signal and the reference property for more than one different level of activity of the human being, and the trend determining means is arranged to determine trends in the medical parameter by analysing the relations obtained for more than one different level of activity. In this way the quality of the trending analysis is improved.

According to yet another advantageous embodiment of the apparatus according to the invention an averaging means is provided to form an average reference signal measured during a certain time period for the reference level of activity of the human being for determining the reference property from the average reference signal. The reference signal can be averaged over long time periods, e.g. months or even years. In this way the influence from temporary disturbances in the reference signal is reduced.

According to another advantageous embodiment of the apparatus according to the invention activity and posture sensors are provided to determine the levels of activity of the patient. As mentioned above the term "activity" includes in this context both true physical activity of the patient as well as his or her posture.

According to still another advantageous embodiment of the apparatus according to the invention calculating means is provided to form the root-mean-square of the sensed signal, viz. the effect in the signal, as the characteristic property.

According to yet another advantageous embodiment of the apparatus according to the invention a frequency analyzer is provided to determine the fundamental and/or harmonics frequencies of the sensed signal as characteristic properties. Frequencies of the fundamental tone and one or more harmonics are then determined, and/or the amplitudes of these tones or harmonics. Also the quotient between e.g. frequencies of the fundamental tone and the first harmonics or the quotient between corresponding amplitudes can be used as characteristic property of the signal.

According to other advantageous embodiments of the apparatus according to the invention a loop generator is connected to two units arranged to determine two different quantities of the sensed signal for plotting related values of the quantities against each other to form a loop for each signal period, and a comparator is connected to the loop generator for comparing the loop with a loop template calculated from the reference signal. One of these quantities can be the signal itself, received from the sensor, and the other one the time derivative of the sensed signal formed by a differentiating means. As characteristic property of the signal can then be chosen e.g. area within the loop, number of turn-arounds in the loop per signal period, the length of the radius to a point on the loop contour corresponding to a specific point in the signal time period, or the angle which this radius forms to an axis of a loop coordinate system.

According to still another advantageous embodiment of the apparatus according to the invention an alerting unit is arranged to be triggered in response to a change in the reference property exceeding a predetermined limit within a predetermine time. Thus if a sufficiently large change is detected in the reference property from e.g. one data collection point to another, this is reported for checking or evaluation, especially if this phenomenon is repeated the patient should be called in for a check.

The invention also relates to an implant for heart failure diagnostics comprising an apparatus as discussed above in which the sensor is arranged to pick up dynamic mechanical information from the heart of the patient and generate a corresponding signal, as well as heart stimulator embodying such an implant and a control means to control stimulation of the heart depending on the determined trends in the medical parameter. Thus by implanting e.g. a piezoelectric sensor or another pressure sensor in the heart of a patient these sensors will pick up dynamic mechanical information which can be used for heart failure diagnostics and heart stimulation control to obtain e.g. true mechanical synchronization, AV- and VV-interval optimization in the operation of the heart.

BRIEF DESCRIPTION OF THE DRAWINGS

FIG. 1 shows an example of a typical qualitative variation of a physiologic parameter of a human being.

FIG. 2 shows a corresponding sensed signal for the variation shown in FIG. 1.

DESCRIPTION OF THE PREFERRED EMBODIMENTS

Dynamic sensing is of particular interest in the field of medical implants, since the sensor most often needs to be designed according to coarse demands inside the body, thus disabling measurements of static parameters. FIG. 1 shows qualitatively the typical variation of a physiologic parameter as a function of time. As can be seen from FIG. 1 the parameter is varying around a certain DC level. A corresponding sensed signal is not available. P-P denotes peak-to-peak.

FIG. 2 shows a corresponding sensed dynamic signal. As appears the variation as a function of time is the same as in FIG. 1, but the used sensor does not pick up the DC component but only the AC component, i.e. the variation information. The sensed signal in FIG. 2 is consequently varying around the zero line of the diagram.

Trending analysis requires, however, some sort of zero or reference level for the necessary comparison analysis. A pseudo-zero or reference level must therefore be determined.

According to the present invention this pseudo-reference level is obtained from a signal sensed by the implanted sensor for a predetermined situation of the patient. This predetermined situation of the patient includes both a predetermined physical activity and a predetermined body position or posture of the patient. In the following the term "activity" of the patient will include the patient's physical activity as well as his or her posture.

For the determination of the reference level in principal any predetermined activity of the patient, e.g. a minimum or a maximum activity, can be used. In the following preferred embodiment the reference level will be determined for a minimum activity of the patient. The reference level is thus preferably determined in night time, when the patient is asleep. The reference level is then preferably obtained from a sensed reference signal which is averaged over some time with the patient asleep. In this way possible influences from posture changes of the patient in sleep state are minimized.

The easiest way of getting a reference level from an averaged sensed signal is to use a clock-triggered function for this purpose, e.g. for using an averaged sensor signal recorded between 00.00 and 02.00 a.m. The reference level can, however, be determined by a more advanced analysis, for instance by using information from a clock, activity and posture sensors.

A mean value of reference levels obtained from this averaged detector signal during a plurality of nights, e.g. for total time periods of months or even years, can also be formed. In this way the reference level, which is needed for the relation analysis, will not be lost in a situation of rapidly worsening conditions of the patient.

Figure 3:
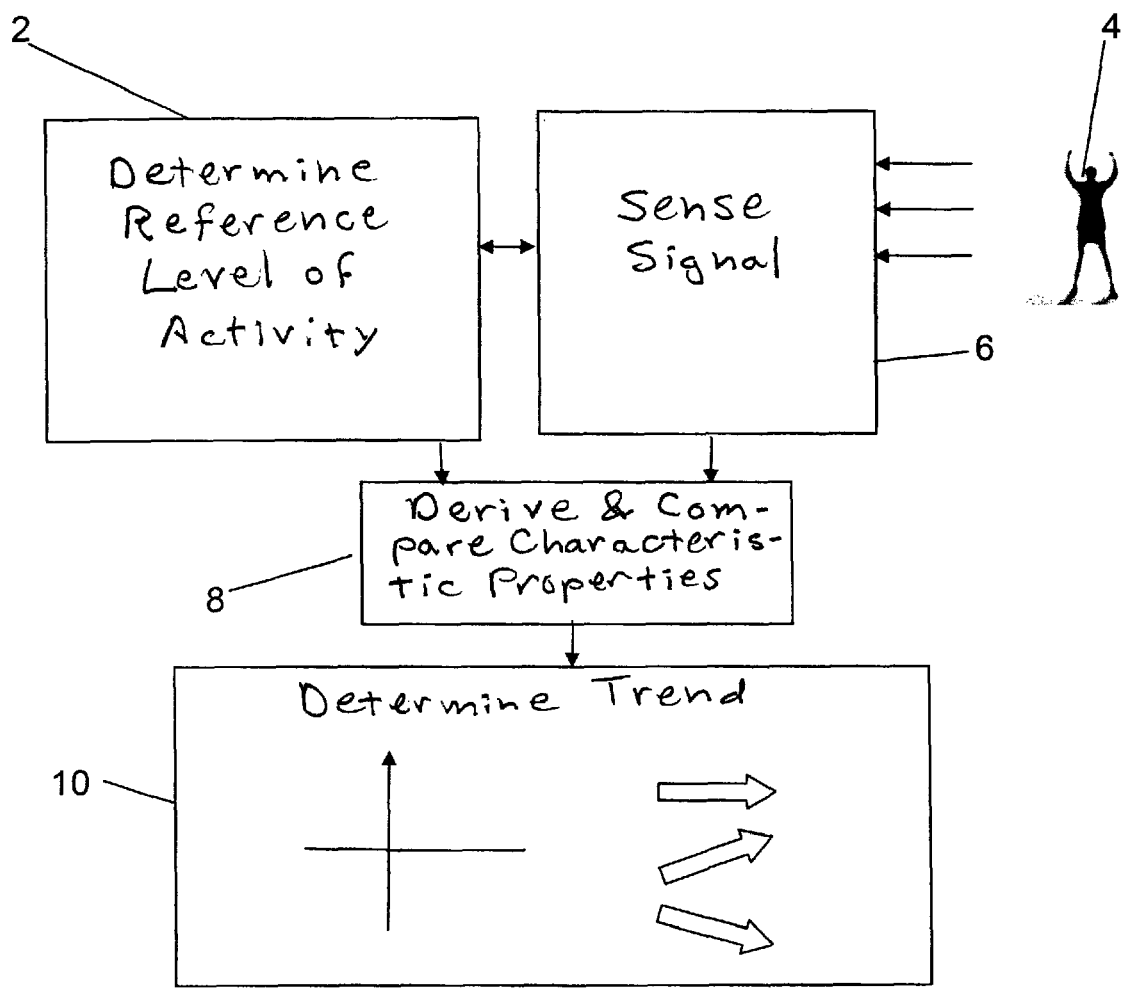
FIG. 3 is a flowchart schematically illustrating an embodiment of the invention.

FIG. 3 is a flow-chart illustrating an example of the procedure in the present invention.

In block 2 the reference level is determined from the sensed signal at a minimum activity (rest or sleep), or another predetermined reference activity, of the patient 4.

In block 6 the signal is sensed by the implanted sensor at every-day-activities or predefined activities of the patient. The sensed signal is stored and/or processed at different times during the day. The signal can be acquired from the sensor continuously or on-demand, controlled by the patient 4, physician, or automatically by a device. In the on-demand mode the implant can be awakened by e.g. a communication device.

Patient hand-held communication devices for patient-interactive therapy with an implanted device is previously known, cf. e.g. the system HeartPod, marketed by the company Savacor, for measuring left atrial pressure interactively with the patient. This system also alerts the patient when it is time to measure. A similar system can be used in connection with the present invention too.

An activity sensor can be provided to sense the patient's activity and for a predetermined activity automatically trigger storage or processing of the sensed signal. Alternatively, the predetermined activity can by defined for instance by 5 steps in a staircase for the patient, or the like.

In block 8 characteristic properties derived from sensed signals are compared with corresponding reference properties of sensed reference signals for determining a relation between the characteristic properties of the sensed signals and the reference properties. These relations can be established for presently sensed signals as well as for previously stored signals.

In block 10, finally, trends are determined in a medical parameter related to the sensed signal by analysing the above-mentioned relations between the characteristic properties of the sensed signal and corresponding reference properties over time. The trend is presented to a physician at e.g. follow-up or is transferred to a remote database for diagnostic purposes.

The horizontal axis of the schematically shown coordinate system in block 10 can represent time, and the vertical axis the magnitude of quantity suitable for representing the trend. The arrows in block 10 indicate examples of determined trends.

The characteristic properties of the sensed signals for the subsequent comparison can be derived in different ways.

The reference signal can be stored as a template to form the reference property with which the sensed signal itself is compared.

The root-mean-square, viz. the effect of the signal, can be calculated as the characteristic property.

Figure 4:
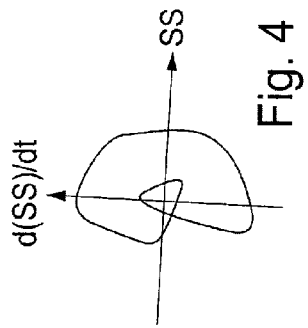
FIGS. 4-6 respectively show examples of the analysis of sensed signals according to different embodiments of the invention.

Two different quantities of the sensed signal can be determined, and a loop generator is provided to plot related quantity values against each other to form a loop for each signal period. An example of such a loop is shown in FIG. 4. In this example a differentiating unit is provided to form the time derivative, d(SS)/dt, of the sensed signal, SS, and the shown loop is formed of related values of d(SS)/dt and SS. Characteristic properties of the signal can then be determined from e.g. the area within the loop, the length of the radius to a specific point A on the loop contour corresponding to a specific time in the signal period, the angle $\alpha$ of the radius to point A, the number of turn-arounds in the loop—two turn-arounds are shown in FIG. 4—and the general morphology of the loop. This kind of signal processing has been previously used for other purposes, see e.g. WO 2002/043587.

The variability of the signal period can be used as characteristic property.

The fundamental and/or the harmonic frequency components of the sensed signal can be used as characteristic properties. Thus the frequencies of the fundamental tone of the signal as well as of its first harmonics can be determined, or the amplitudes, of these tones.

Figure 5:
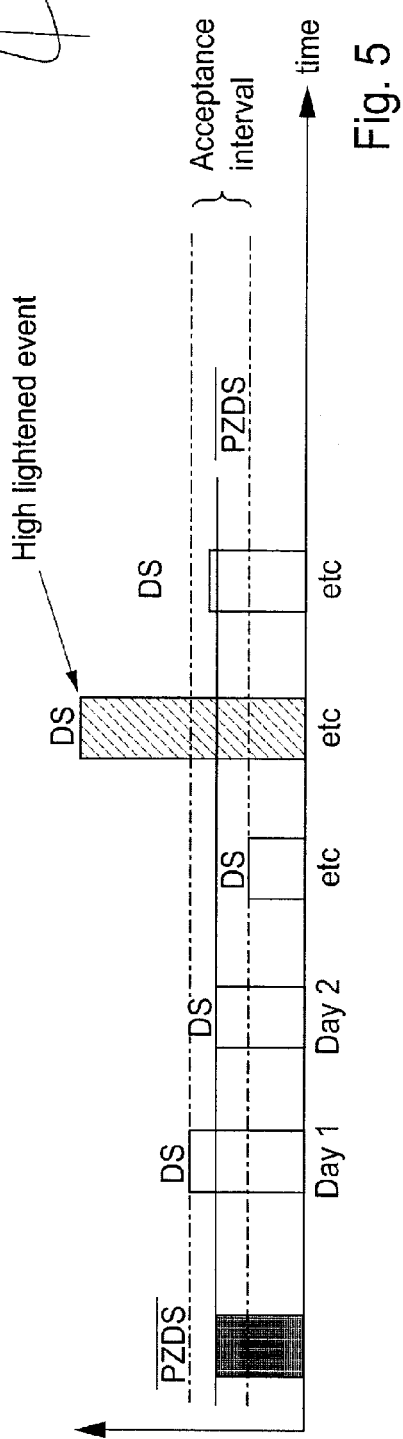
Figure 6:
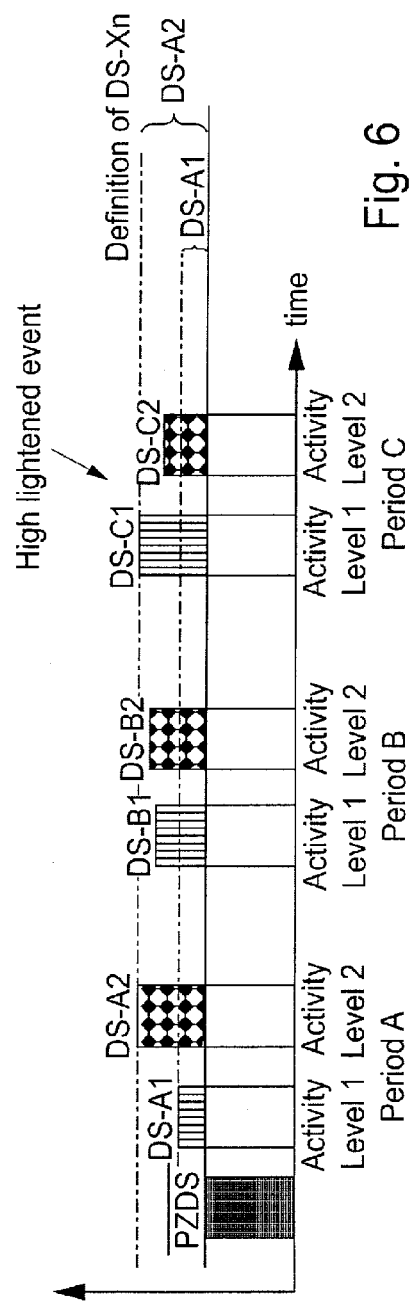

Relation between characteristic properties of the sensed signal and corresponding reference properties are stored and displayed at follow-up or distributed to a central diagnostic unit at a hospital for evaluation, as explained above. FIGS. 5 and 6 illustrate two examples of the comparison analysis over time of sensed signal and reference level. The vertical axis represent a quantity corresponding to the signal level.

In FIG. 5 signals DS are sensed for one defined activity level of the patient. The reference level, which is an average value of DS during a certain time period of substantially constant level of activity of the patient, is denoted by PZDS, represented by the first bar to the left in the figure. Signals situated within an acceptance interval around PZDS are considered as normal according to preset criteria. For a couple of days, Day 1, Day 2, etc. the sensed signal DS is within the acceptance interval. Then a sensed signal DS appears, the sectioned bar, which significantly exceeds the upper limit of the acceptance interval. This event is highlightened for subsequent observations. Thereafter sensed signals follow which fall within the acceptance interval.

FIG. 6 illustrates an example of the comparison analysis in a situation where signals are sensed for two different pre-defined levels of activity, Activity level 1 and Activity level 2, of the patient. In this case the inter-relation levels $(DS-X_{n+1})-(DS-X_n)$ is trended, $DS-X_n$ denoting the signal at period X and activity level number n. Thus $DS-A_1$ denotes the signal for activity level 1 in period A, $DS-A_2$ the signal for activity level 2 in period A, $DS-B_1$ the signal for activity level 1 in period B, etc. In this example the situation is considered as "normal", provided the criterion $(DS-X_1)<(DS-X_2)$ is fulfilled. From the figure it appears that this criterion is satisfied for Period A and Period B but not for Period C which event is consequently highlighted for evaluation.

Figure 7:
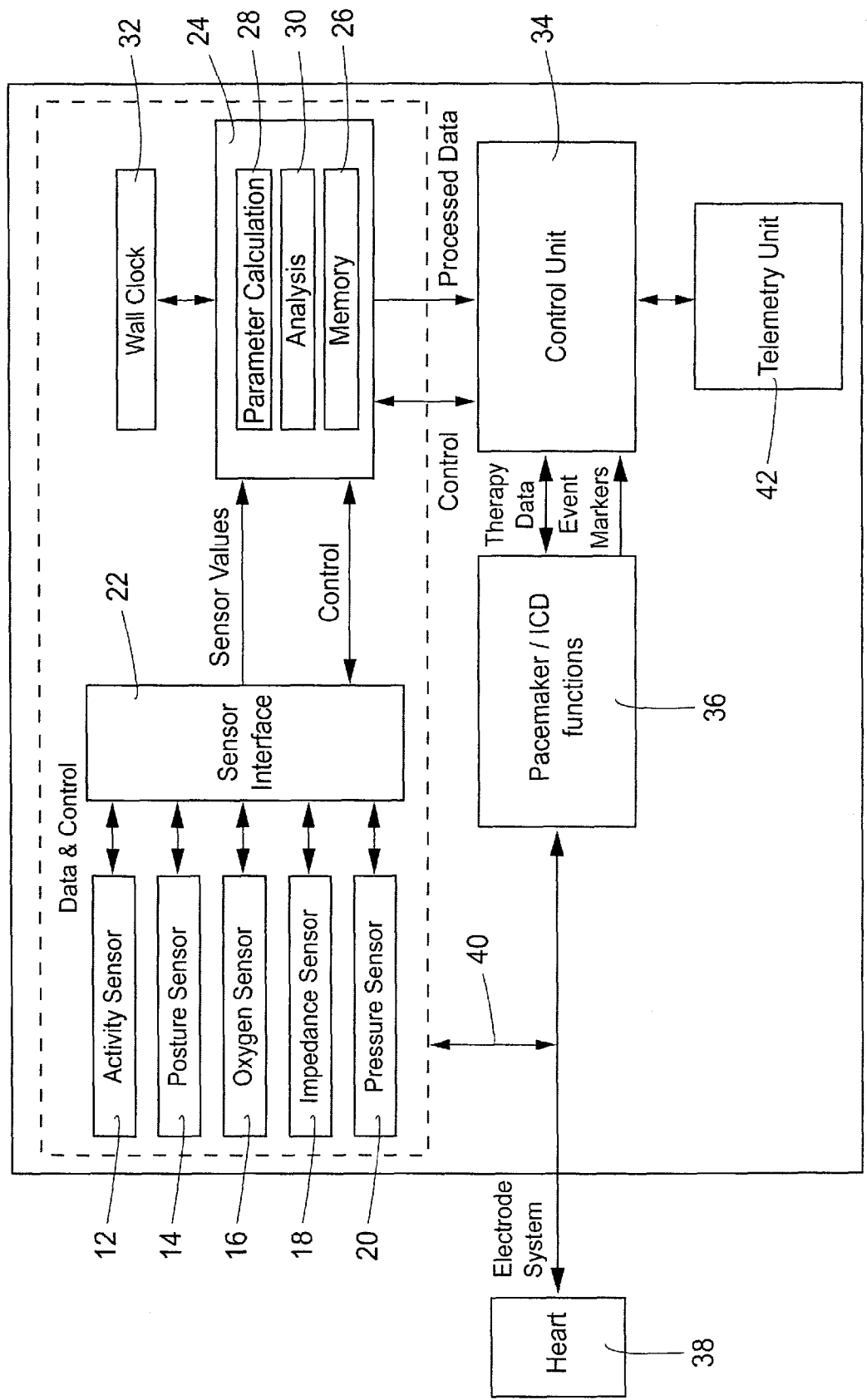
FIG. 7 is a block diagram of an embodiment of the invention implemented in a pacemaker or an implantable cardio-defibrillator.

FIG. 7 is a block diagram of an implantable pacemaker or ICD provided with an apparatus according to the invention, located within the dashed line in the figure.

A number of different, implantable sensors can be used in the present invention, viz. an activity sensor 12, a posture sensor 14, an oxygen sensor 16, an impedance sensor 18 and a pressure sensor 20. One or more of the sensors are connected through a sensor interface 22 to a signal processing, calculating and analysing device 24. Signals or sensor values from the sensor 12, 14, 16, 18, 20 are supplied to the device 24 for storing in a memory 26 for subsequent use or processed and supplied to a calculation unit 28 for calculation of one or more characteristic properties. The calculated characteristic properties can be supplied to the analysis unit 30 for establishing a relation to a stored reference property and comparing this relation with stored relations, obtained from previous measurements for determining trends in a medical parameter related to the sensed signal. Alternatively, the calculated characteristic properties can be stored in the memory 26 for later trending analysis.

A clock 32 is connected to the device 24 for setting the time for e.g. reading, through the sensor interface 22, sensed values to the device 24 for processing and analysis. The clock can also control the time for the trending analysis based on stored data. In case of time averaging of the sensed signal the clock 32 controls the period for the averaging, and the clock 32 also controls the transfer of trend data to the control unit 34 for the pacemaker or ICD 36.

The control unit 34 controls the therapy, i.e. the cardiac stimulation delivered by the pacemaker 36 via electrodes implanted in a patient's heart 38 by exchange of therapy data between the control unit 34 and the pacemaker 36.

The arrow 40 indicates that the sensors are preferably connected to the patient's heart 38 through the pacemaker electrode system Detected cardiac event markers are transferred to the control unit 34 and there is a feedback from the control unit 34 to the processing and analyzing device 24.

A telemetry unit 42 is provided for reading out data from the trending analysis at follow-up or for transfer to a central diagnostic station for evaluation. Also therapy data and other information can be communicated by this unit between the implant and external equipments.

Although modifications and changes may be suggested by those skilled in the art, it is the intention of the inventors to embody within the patent warranted heron all changes and modifications as reasonably and properly come within the scope of their contribution to the art.

The invention claimed is:

1. An apparatus for obtaining variation over time of a medical parameter of a human being, comprising:
   a sensor configured for in vivo implantation in a human being to sense a periodic physiological signal in the human being;
   a controller configured to operate said sensor to obtain said sensed signal for at least one predetermined level of activity of the human being and to obtain a sensed reference signal from the sensor for a predetermined reference level of said activity;

a first quantity determining unit that determines a first quantity from each of said sensed signal said sensed reference signal;

a second quantity determining unit that determines a second quantity from each of said sensed signal and said sensed reference signal;

a loop generator that plots related values of said first and second quantities for said reference signal to generate a loop template from said reference signal and that plots related values of said first and second quantities for said sensed signal to generate a loop in each period of said signal in a coordinate system having an origin and a coordinate system axis;

comparator circuitry that compares a loop characteristic of said loop in each period of said signal and in said loop template to determine a relation between said sensed signal and said sensed reference signal for each period, said loop characteristic being selected from the group consisting of an angle that a radius of the origin to a predetermined point on the loop contour, corresponding to a predetermined time in the period of said sensed signal, forms with respect to said coordinate system axis in each of said loop and said loop template, and a number of turn-arounds within each loop and said loop template during each period of said sensed signal; and a trend determining unit configured to determine a trend in a medical parameter of the human being by analyzing said relation obtained for said different periods.

2. An apparatus as claimed in claim 1 wherein said sensor is a pressure sensor.

3. An apparatus as claimed in claim 1 wherein said sensor is a piezoelectric sensor that senses mechanical activity of the human being.

4. An apparatus as claimed in claim 1 wherein said controller is configured to operate said sensor to obtain said sensed reference signal at a reference level of activity that is a state of minimum activity for the human being.

5. An apparatus as claimed in claim 1 comprising a storage unit wherein said loops for said respectively different periods are stored.

6. An apparatus as claimed in claim 1 wherein said comparator circuitry is configured to determine said relation for multiple, different levels of said activity, and wherein said trend determining unit is configured to determine said trend in said medical parameter by analyzing the respective relations for said multiple, different levels of said activity.

7. An apparatus as claimed in claim 1 comprising at least one of a posture sensor and an activity level sensor connected to said controller, that provide respective additional sensor signals to said controller to identify said level of activity and said reference level of activity.

8. An apparatus as claimed in claim 1 wherein said first quantity determining unit uses the sensed signal itself for the sensed reference signal itself as said first quantity, and wherein said second quantity determining unit generates a time derivative of the sensed signal or a time derivative of the sensed reference signal as said second quantity.

9. An apparatus as claimed in claim 1 comprising an alerting unit that is triggered to emit a humanly perceptible signal upon said trend determining unit identifying a change of said relation exceeding a predetermined limit within a predetermined time.

10. A method for obtaining variation over time of a medical parameter of a human being, comprising the steps of:

with a sensor configured for in vivo implantation in a human being, sensing a periodic physiological signal in the human being;

operating said sensor to obtain said sensed signal for at least one predetermined level of activity of the human being and to obtain a sensed reference signal from the sensor for a predetermined reference level of said activity;

automatically electronically determining a first quantity from each of said sensed signal said sensed reference signal;

automatically electronically determining a second quantity from each of said sensed signal and said sensed reference signal;

in a loop generator, plotting related values of said first and second quantities for said reference signal to generate a loop template from said reference signal and that plots related values of said first and second quantities for said sensed signal to generate a loop in each period of said signal in a coordinate system having an origin and a coordinate system axis;

in comparator circuitry, comparing a loop characteristic of said loop in each period of said signal and in said loop template to determine a relation between said sensed signal and said sensed reference signal for each period, said loop characteristic being selected from the group consisting of an angle that a radius of the origin to a predetermined point on the loop contour, corresponding to a predetermined time in the period of said sensed signal, forms with respect to said coordinate system axis in each of said loop and said loop template, and a number of turn-arounds within each loop and said loop template during each period of said sensed signal; and automatically electronically determining a trend determining unit configured to determine a trend in a medical parameter of the human being by analyzing said relation obtained at said respectively different times.

11. A method as claimed in claim 10 comprising implanting a pressure sensor as said sensor.

12. A method as claimed in claim 10 comprising implanting a piezoelectric sensor that senses mechanical activity of the human being as said sensor.

13. A method as claimed in claim 10 comprising operating said sensor to obtain said sensed reference signal at a reference level of activity that is a state of minimum activity for the human being.

14. A method as claimed in claim 10 comprising electronically storing said loops for respectively different periods.

15. A method as claimed in claim 10 comprising determining said relation for multiple, different levels of said activity, and determining said trend in said medical parameter by analyzing the respective relations for said multiple, different levels of said activity.

16. A method as claimed in claim 10 comprising, with at least one of a posture sensor and an activity level sensor providing respective additional sensor signals that identify said level of activity and said reference level of activity.

17. A method as claimed in claim 10 comprising using the sensed signal itself for the sensed reference signal itself as said first quantity, and generating a time derivative of the sensed signal or a time derivative of the sensed reference signal as said second quantity.

18. A method as claimed in claim 10 comprising triggering emission of a humanly perceptible signal upon identifying a change of said relation exceeding a predetermined limit within a predetermined time.

19. A heart stimulator comprising:

a sensor configured for in vivo implantation in a human being to sense a periodic physiological signal in the human being;

a controller configured to operate said sensor to obtain said sensed signal for at least one predetermined level of activity of the human being and to obtain a sensed reference signal from the sensor for a predetermined reference level of said activity;

a first quantity determining unit that determines a first quantity from each of said sensed signal said sensed reference signal;

a second quantity determining unit that determines a second quantity from each of said sensed signal and said sensed reference signal;

a loop generator that plots related values of said first and second quantities for said reference signal to generate a loop template from said reference signal and that plots related values of said first and second quantities for said sensed signal to generate a loop in each period of said signal in a coordinate system having an origin and a coordinate system axis;

comparator circuitry that compares a loop characteristic of said loop in each period of said signal and in said loop template to determine a relation between said sensed signal and said sensed reference signal for each period, said loop characteristic being selected from the group consisting of an angle that a radius of the origin to a predetermined point on the loop contour, corresponding to a predetermined time in the period of said sensed signal, forms with respect to said coordinate system axis in each of said loop and said loop template, and a number of turn-arounds within each loop and said loop template during each period of said sensed signal; and a trend determining unit configured to determine a trend in a medical parameter of the human being by analyzing said relation obtained at said respectively different times; and stimulating circuitry configured for interaction with the heart of the human being to stimulate the heart dependent on said trend in said medical parameter.

20. A heart stimulator as claimed in claim 19 wherein said heart stimulator comprises an intracorporeal communication unit configured to transmit signals representing said relation, determined for said different periods, to an extracorporeal receiver.

* * * * *